United States Patent [19]

Romano et al.

[11] Patent Number: 4,623,705

[45] Date of Patent: Nov. 18, 1986

[54] PROCESS FOR SYNTHESIZING ALLYL CARBONATES BY POLYHYDRIC ALCOHOLS AND THEIR DERIVATIVES

[75] Inventors: Ugo Romano, Vimercate; Giuseppe Iori, San Donato Milanese, both of Italy

[73] Assignee: Anic S.p.A., Palermo, Italy

[21] Appl. No.: 694,266

[22] Filed: Jan. 24, 1985

Related U.S. Application Data

[60] Division of Ser. No. 374,331, May 3, 1982, Pat. No. 4,508,656, which is a continuation of Ser. No. 240,119, Mar. 3, 1981, abandoned.

[30] Foreign Application Priority Data

Mar. 5, 1980 [IT] Italy ................. 20351 A/80

[51] Int. Cl.$^4$ ............ C08F 18/24; C08F 118/24; C08F 218/24; C08F 2/00
[52] U.S. Cl. .................................. 526/75; 526/314
[58] Field of Search .................. 526/314; 260/453

[56] References Cited

U.S. PATENT DOCUMENTS

| | | | |
|---|---|---|---|
| 2,387,934 | 10/1945 | Muskat | 526/314 |
| 2,403,113 | 7/1946 | Muskat | 526/314 |
| 2,787,632 | 4/1957 | Stevens | 260/463 |
| 2,789,968 | 4/1957 | Reynolds | 260/77.5 |
| 2,844,448 | 7/1958 | Heisler et al. | 44/70 |
| 3,497,478 | 2/1970 | Field | 260/77.5 |
| 3,784,578 | 1/1974 | Swodenk | 260/410.9 |
| 4,005,121 | 1/1977 | Senet | 260/463 |
| 4,033,933 | 7/1977 | Bruns et al. | 260/463 |
| 4,062,884 | 12/1977 | Romano et al. | 260/463 |
| 4,144,262 | 3/1979 | Stevens | 260/463 |
| 4,217,438 | 8/1980 | Brunelle et al. | 528/202 |
| 4,273,726 | 6/1981 | Altuglu | 260/463 |
| 4,293,503 | 10/1981 | Young | 260/463 |
| 4,307,032 | 12/1981 | Krimm et al. | 260/463 |
| 4,349,486 | 9/1982 | Brunelle et al. | 260/463 |
| 4,563,416 | 1/1986 | Shipota et al. | 526/314 |

FOREIGN PATENT DOCUMENTS 2749754 5/1979 Fed. Rep. of Germany.

Primary Examiner—Joseph L. Schofer
Assistant Examiner—Peter F. Kulkosky
Attorney, Agent, or Firm—Morgan & Finnegan

[57] ABSTRACT

The application relates to a process for synthesizing carbonic allyl esters from polyhydric alcohols, which are reacted with diallyl carbonate in the presence of a basic catalyst, which can be chosen from sodium hydroxide, sodium carbonate, sodium alcoholate, organic bases or basic ion exchange resins.

The final products obtained differ according to the ratio of the components of the starting mixture. Thus, in the case of diols with a diallyl carbonate/diol ratio greater than or equal to 10, the resultant product is constituted by the bis allyl carbonate of the diol together with a quantity of less than or equal to 10% of oligomers represented mainly by dimers. If the ratio is less than 10, the percentage of oligomers rises until, in the case of an approximately stoichiometric ratio, it reaches a value close to 70% of the reaction product.

12 Claims, No Drawings

PROCESS FOR SYNTHESIZING ALLYL CARBONATES BY POLYHYDRIC ALCOHOLS AND THEIR DERIVATIVES

This is a division of application Ser. No. 374,331 filed May 3, 1982, now U.S. Pat. No. 4,508,656, which is a continuation of application Ser. No. 240,119, filed Mar. 3, 1981, now abandoned.

This invention relates to a process for synthesising carbonic allyl esters of formula

particularly starting from polyhydric alcohols, which consists of reacting diallyl carbonate with the alcohol concerned in the presence of a basic catalyst. The product thus obtained is then used in post-modification or polymerisation reactions to prepare valuable derivatives of varied use, these derivatives constituting an integral part of the present invention. It is well known that bis allyl carbonates of glycols and/or polyglycols are commonly prepared by reacting allyl chloroformate with the glycol, or alternatively the glycol-bis-chloroformate with the allyl alcohol, the reaction always taking place in the presence of an acceptor for the hydrochloric acid which is released, as described for example in the U.S. Pat. Nos. 2,370,565 and 2,592,058. The reactions stated are such that the products obtained are frequently coloured when in the crude state, and are thus unsuitable for immediate use in that which is considered one of the main fields of application of these compounds, namely raw materials for forming organic glass substitutes for optical purposes. The purification comprises stages such as decoloration and/or distillation under reduced pressure, which considerably affect the economics of the process and a priori cannot ensure the subsequent good quality of the product.

In this respect, the presence of chloroformate among the starting materials leads to a constant presence of chlorinated impurities in the final products even after purification, and these impurities characterise the specific properties of the product, so as to make the subsequent treatment which precedes their practical use sometimes problematic.

As stated, the present invention relates to an improved process for synthesising allyl carbonates of polyhydric alcohols, mainly glycols, which enables the final products to be obtained without any of the aforesaid drawbacks.

The process comprises reacting together the starting substrates (polyols and allyl carbonate) at a temperature of between 50° and 150° C. and at a pressure variable between atmospheric pressure and 10 mmHg.

The starting compounds are brought into contact in the presence of a basic catalyst, which is introduced in a quantity variable between 0.1 ppm and 1% by weight with respect to the alcohol.

The molar ratio of the diallyl carbonate to the alcohol varies between 2 and 20.

The polyhydric alcohols used can be chosen from a wide range, for example ethylene glycol, propylene glycol, diethylene glycol, triethylene glycol, tetraethylene glycol, butanediol, hexanediol, glycerol etc.

The catalyst itself can be chosen from NaOH, Na$_2$CO$_3$, sodium alcoholate, organic bases or basic ion exchange resins. The reaction can be carried out using commercially available products as the starting substances without further purification.

The final products are absolutely colourless and free from those impurities which, as stated, lead to the disadvantages of the products obtained according to the known art.

With the present method of synthesis, either the pure ester or a mixture thereof with oligomers constituted by chains of allyl terminated alcohol polycarbonate is obtained, according to the diallyl carbonate/polyhydric alcohol molar ratio. The structure of the monomer and oligomers in the case of glycol is as follows:

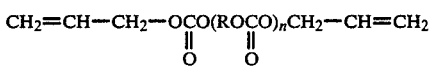

where n lies between 1 and 10, and R represents a hydrocarbon radical.

If the diallyl carbonate/glycol ratio is greater than or equal to 10, the final product is formed by the allyl carbonate of the glycol with a quantity of less than or equal to 10% of oligomers mainly represented by dimers (n=2). If the ratio is less than 10, the oligomer percentage rises until, for an approximately stoichiometric ratio, it reaches a value close to 70% of the reaction product.

The density and viscosity of the product increases in relation to the increase in oligomer concentration.

By way of example, some characteristics of the product obtained from diallyl carbonate (DAC) and diethylene glycol (DEG) for various molar ratios are as follows:

| Mol ratio. DAC/DEG | % mon. | % olig. | Density | Viscos. cst (25° C.) |
|---|---|---|---|---|
| 12 | 94 | 6 | 1.148 | 12 |
| 8 | 81 | 19 | 1.151 | 17 |
| 5 | 60 | 40 | — | 19 |
| 3.5 | 52 | 48 | — | 32 |
| 2.5 | 40 | 60 | — | 64 |

The Saybolt colour is constantly greater than +30, and the UV-visible absorbency is as follows:

| nM | 300 | 350 | 400 | 450 | 600 | 700 |
|---|---|---|---|---|---|---|
| Absorbency | 0.2 | 0.04 | 0 | 0 | 0 | 0 |

The only volatile impurities (BP<150° at 5 mmHg) which can be present are traces of diallyl carbonate (<1%).

According to one embodiment of the process of the invention, the reaction between diallyl carbonate and the polyhydric alcohol is carried out in a vessel fitted with a stirrer and distillation column for removing the allyl alcohol released by the transesterification reaction.

The carbonate and alcohol are thus fed in the required molar ratio, and the environment is deaerated before introducing the catalyst. With diethylene glycol, for example, the catalyst is added in dispersed solid form or in preferably alcoholic solution to the extent of 0.5 to 10 ppm by weight of Na with respect to the diethylene glycol used.

Heating is then started under a residual pressure of 150-200 mmHg, taking particular care to have no infiltration of air. The allyl alcohol, which is released to the extent of 2 moles per mole of fed glycol, rapidly distils over, and the reaction is terminated in about 1 hour. The residual vacuum is then gradually increased to remove the excess of diallyl carbonate. The diallyl carbonate which remains in the product is a function of the degree of vacuum at which this removal is carried out. In particular, if operating at 10 mmHg, the diallyl carbonate remaining in the product is less than 1%.

The residual product, after filtering and possibly washing with water and dehydrated, is perfectly clear, colourless and suitable for the application for which it is intended. The esters thus obtained can for example be directly used in radical polymerisation reactions in bulk, to give products of high technological value.

In the particular case of polymerisation, this is carried out in the presence of initiators or free radicals of peroxide or peroxycarbonate type in a percentage variable between 1 and 12% with respect to the monomer, at a temperature of between 30° and 120° C. for a time variable from a few hours to several hours.

The moulds of the required shape, which are usually of carefully machined glass or steel fitted with an elastic gasket in order to follow the volume contraction of the product under polymerisation, are completely filled with the monomer to which the filtered and deaerated catalyst is added. They are then placed in an air or water oven and left there to polymerise for a time and temperature cycle which vary with the dimensions of the mould, the thickness, the type and percentage of catalyst.

Generally, an increasing temperature of between 40° and 100° C. is maintained for a time varying from a few hours to several tens of hours.

At the end of the determined cycle, the product, which is now at the termination of cross-linkage, can be released from the mould and subjected to final hardening by heat treatment in air ovens at a temperature of about 90°–110° C. for a time of between 1 hour and a few hours. The products thus treated attain a very high and constant quality standard. The measurement of the chemical and physical characteristics of the various products demonstrates a complete and properly conducted polymerisation cycle.

Using the described polymerisation method, test pieces uniform in terms of shape and dimensions were obtained, and these were then subjected to measurements of optical-mechanical properties significant for the main use for which these polymers are intended, i.e. as glass substitutes.

The polymerisation for example of the various samples of carbonic allyl esters of diethylene glycol always followed the scheduled temperature and duration cycles, and never gave rise to any difficulties during cross-linkage, or on opening the moulds, such as breakages or separation difficulties. The transmission values for light from 350 to 700 nM are constantly above 89%.

The Rockwell hardness measured on test pieces deriving from distilled ester is maintained at around values of M 100, while falling to values of M 85 for test pieces originating from ester containing 70% of monomer and 30% of oligomer carbonates, and reducing to values of M 50 for test pieces originating from ester in which the oligomer carbonates represent 60% of the product.

The resistance to scratching is high for all samples, and this appears substantially independent of the percentage of oligomers in the initial allyl carbonate ester.

However, the impact resistance increases considerably with this percentage. The bending modulus is also constant within certain limits, and is reduced for test pieces originating from esters containing 60% of oligomers.

EXAMPLE 1

12 moles of diallyl carbonate and 1 mole of diethylene glycol are mixed at ambient temperature under an inert atmosphere in a 3 neck flask fitted with a thermometer, stirrer and distillation column. When mixing is complete, 0.05 millimoles of powdered NaOH are added, and heating is commenced at a residual pressure of 150 mmHg.

After the two moles of released allyl alcohol have been withdrawn as overheads, the residual pressure is lowered to 2 mmHg in order to remove the excess diallyl carbonate. A perfectly colourless product (Saybolt colour > +30) is obtained on the bottom, and is composed of

| Diallyl carbonate | 0.5% by weight |
|---|---|
| Diethylene glycol bis allyl carbonate | 89.85% by weight |
| Oligomers | 9.65% by weight |

This product is washed with water until neutral, dried and filtered. The yield with respect to the fed diethylene glycol is total.

EXAMPLE 2

The reaction is carried out as in example 1, with the difference that 0.005 millimoles of sodium methylate are used as catalyst. The sodium methylate was introduced as a 30% methanol solution, again under an inert atmosphere.

When the reaction was finished, the colourless bottom liquid was washed, dried and filtered.

The yield is total with respect to the fed diethylene glycol. The composition of the product is:

| Diallyl carbonate | 0.5 |
|---|---|
| Diethylene glycol bis allyl carbonate | 91.5 |
| Oligomers | 8.0 |

EXAMPLE 3

The reaction is carried out as in example 2, the only difference being that the catalyst was introduced as a solid, and after removing the excess of diallyl carbonate the perfectly colourless bottom product is only filtered. Yield and composition as in example 2.

EXAMPLE 4

The reaction is carried out as in example 2, except that the diallyl carbonate:diethylene glycol molar ratio was 10:1. The perfectly colourless bottom product is washed, dehydrated, filtered and analysed. The yield with respect to the fed diethylene glycol is total. The composition is as follows:

| Diallyl carbonate | 0.5 |
|---|---|
| Diethylene glycol bis allyl carbonate | 85.3 |
| Oligomers | 14.2 |
| Viscosity at 25° C. 15.15 cst. | |

EXAMPLES 5-8

The reaction described in example 4 is carried out at the following diallyl carbonate/diethylene glycol ratios.

| Example | Diallyl carbonate/diethylene glycol ratio | Composition Monomer | Oligomers | Viscosity cst at 25° C. |
|---|---|---|---|---|
| 5 | 8:1 | 81 | 19 | 0.17 |
| 6 | 5:1 | 60 | 40 | 19 |
| 7 | 3.5:1 | 52 | 48 | 32 |
| 8 | 2.5:1 | 40 | 60 | 64 |

EXAMPLE 9

The reaction is carried out as in example 2, the only difference being that 0.01 millimoles of metal sodium per mole of diethylene glycol are used as catalyst.

After the excess diallyl carbonate has been removed, a slightly yellow bottom product of identical composition to the product of test 2 remains.

Purification is carried out by distilling at a residual pressure of 2 mmHg and a temperature of 160° C.

Perfectly colourless diethylene glycol bis allyl carbonate is obtained, with a yield of 80% with respect to the fed diethylene glycol.

A very viscous yellow product remains in the bottom, consisting mainly of allyl terminated oligomer carbonates.

EXAMPLES 10-13

The peroxide-based initiator was added to the esters obtained in the tests of the preceding examples, which were then polymerised in glass moulds fitted with flexible gaskets in air ovens or water baths at a temperature increasing between 40° and 90° C. for a time of between 2 and 24 hours according to the type and concentration of initiator. Test pieces were obtained, of which both the optical properties and physicomechanical properties were measured.

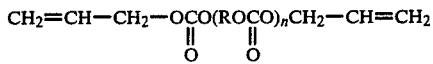

in which R is a hydrocarbon radical and n is a number from 1 to 10 and (2) subjecting said mixture to radical polymerization.

2. A process according to claim 1 wherein said polymerization is carried out in the presence of a radical initiator the quantity of which is between 1 and 12% by weight with respect to the carbonate.

3. A process according to claim 2 wherein said radical initiator is selected from the group consisting of peroxides, peroxycarbonates and peroxycarbamides.

4. A process according to claim 1 wherein said polymerization is carried out at a temperature of between 30° and 120° C.

5. A process according to claim 1 wherein said initial reactants are a mixture of monomers and oligomers of diethylene glycol bis allyl carbonate.

6. A process according to claim 5 wherein the monomer component is greater than 40% by weight of the initial reactants.

7. A process according to claim 1 wherein the molar ratio of diallyl carbonate to polyhydric alcohol is between 2 and 20.

8. A process for preparing polymers suitable for use as glass substitutes comprising (1) reacting diallyl carbonate and diethylene glycol in a molar ratio from between 2.5:1 and 12:1 in the presence of a basic catalyst thereby obtaining a mixture of monomers and oligomers of diethylene glycol bis allyl carbonate and (2) subjecting said mixture to radical polymerization, wherein the resultant polymers have a transmission value for light from 350 to 700 NM greater than 89%.

9. A process according to claim 7 wherein said polymerization is carried out in the presence of a radical initiator the quantity of which is between 1 and 12% by weight with respect to the carbonate.

10. A process according to claim 8 wherein said radi-

| Allyl carbonate | Optical properties Visible Transmission (%) (1) | Physico-mechanical properties | | | | | |
|---|---|---|---|---|---|---|---|
| | | ROCKWELL HARDNESS M (2) | IZOD IMPACT NOTCHED J/m (3) | IZOD IMPACT UNNOTCHED KJ/M² (4) | ELASTIC MODULUS MPA (5) | SCRATCH RESISTANCE (6) | TABER ABRASION % HAZE (7) |
| Ex. 9 | 90.5 | M 97 | 28 | 170 | 2200 | 32 | 35 |
| Ex. 2 | 90.0 | M 90 | 35 | 230 | 2100 | 32 | 33.5 |
| Ex. 5 | 91.0 | M 83 | 50 | 230 | 2100 | 29 | — |
| Ex. 8 | 90.8 | M 50 | 40 | 320 | 700 | 24 | — |
| Polycarbonate from bisphenol A | — | — | — | — | — | 6 | |
| Polystyrene | — | — | — | — | — | 6 | |

(1) Thickness 2.7 m at 400-700 NM
(2) ASTM D 785
(3) ASTM D 256
(4) ASTM D 256 MODIF
(5) ASTM D 790
(6) INTERNAL METHOD
(7) CS10 ABRASIVE WHEEL, load 0.5 kg.

We claim:

1. A process for preparing polymers suitable for use as optical glass substitutes comprising (1) reacting diallyl carbonate with a polyhydric alcohol in the presence of a basic catalyst to obtain a mixture of monomers and oligomers of allyl carbonates of polyhydric alcohols of the following formula:

cal initiator is selected from the group consisting of peroxides, peroxycarbonates and peroxycabamides.

11. A process according to claim 7 wherein said polymerization is carried out at a temperature of between 30° and 120° C.

12. A process according to claim 7 wherein the monomer component of the mixture is greater than 40% by weight of the mixture of monomers and obligomers.

* * * * *